(12) United States Patent
Kase et al.

(10) Patent No.: US 9,131,834 B2
(45) Date of Patent: Sep. 15, 2015

(54) ENDOSCOPE

(71) Applicant: OLYMPUS CORPORATION, Tokyo (JP)

(72) Inventors: Seigo Kase, Hino (JP); Yasuhito Kura, Hachioji (JP); Yuji Sakamoto, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 159 days.

(21) Appl. No.: 13/719,885

(22) Filed: Dec. 19, 2012

(65) Prior Publication Data

US 2013/0109917 A1    May 2, 2013

Related U.S. Application Data

(63) Continuation of application No. 13/084,055, filed on Apr. 11, 2011, now Pat. No. 8,343,043, which is a continuation of application No. PCT/JP2010/068724, filed on Oct. 22, 2010.

(30) Foreign Application Priority Data

Nov. 6, 2009 (JP) ................................ 2009-255187

(51) Int. Cl.
*A61B 1/06* (2006.01)
*A61B 1/00* (2006.01)
(Continued)

(52) U.S. Cl.
CPC ......... *A61B 1/00181* (2013.01); *A61B 1/00045* (2013.01); *A61B 1/0052* (2013.01);
(Continued)

(58) Field of Classification Search
CPC .... A61B 1/00096; A61B 1/06; A61B 1/0607; A61B 1/0612; A61B 1/0623; A61B 1/07
USPC .......... 600/170, 171, 176, 177, 109, 160, 182
See application file for complete search history.

(56) References Cited

U.S. PATENT DOCUMENTS

| 3,548,808 | A | 12/1970 | Takahashi et al. |
| 5,700,236 | A | 12/1997 | Sauer et al. |

(Continued)

FOREIGN PATENT DOCUMENTS

| EP | 1 769 718 A1 | 4/2007 |
| JP | S53-126386 | 10/1978 |

(Continued)

OTHER PUBLICATIONS

International Search Report dated Oct. 22, 2010.
(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

An endoscope includes: a distal end portion provided at a distal end of an insertion portion; a front-view observation window for observing an insertion direction of the distal end portion, which is provided facing toward the insertion direction; a lateral-view observation window for observing a circumferential direction of the distal end portion, which is formed along the outer circumferential lateral surface and has a lateral observation field of view; a light-emitting member having an emission end surface for emitting light in a distal end direction of the distal end portion; a groove portion formed on the outer circumferential lateral surface of the distal end portion so as to be longer than the emission end surface of the light-emitting member along the circumferential direction of the outer circumferential lateral surface of the distal end portion and opposed to the emission end surface, on a proximal end side with respect to the lateral-view observation window; a plurality of particles for scattering light arranged in the groove portion; and a transparent infill filled between the plurality of particles.

11 Claims, 7 Drawing Sheets

(51) Int. Cl.
*A61B 1/07* (2006.01)
*A61B 1/12* (2006.01)
*A61B 1/005* (2006.01)
*A61B 1/015* (2006.01)
*A61B 1/04* (2006.01)

(52) U.S. Cl.
CPC ......... *A61B1/00096* (2013.01); *A61B 1/00114* (2013.01); *A61B 1/00117* (2013.01); *A61B 1/00177* (2013.01); *A61B 1/015* (2013.01); *A61B 1/04* (2013.01); *A61B 1/0615* (2013.01); *A61B 1/0623* (2013.01); *A61B 1/0676* (2013.01); *A61B 1/07* (2013.01); *A61B 1/126* (2013.01)

(56) References Cited

U.S. PATENT DOCUMENTS

| | | | |
|---|---|---|---|
| 5,782,751 | A | 7/1998 | Matsuno |
| 5,961,445 | A | 10/1999 | Chikama |
| 6,053,862 | A | 4/2000 | Ono |
| 6,261,226 | B1 | 7/2001 | McKenna et al. |
| 6,537,209 | B1 | 3/2003 | Pinkhasik et al. |
| 6,887,196 | B2 | 5/2005 | Arai et al. |
| 7,267,647 | B2 | 9/2007 | Okada et al. |
| 7,559,890 | B2 | 7/2009 | Wallace et al. |
| 7,922,655 | B2 | 4/2011 | Yasushi et al. |
| 2004/0254424 | A1 | 12/2004 | Simkulet et al. |
| 2006/0217593 | A1 | 9/2006 | Gilad et al. |
| 2007/0118020 | A1 | 5/2007 | Miyagi et al. |
| 2007/0197875 | A1 | 8/2007 | Osaka |
| 2007/0203396 | A1 | 8/2007 | McCutcheon et al. |
| 2007/0224571 | A1 | 9/2007 | Watson |
| 2008/0045797 | A1 | 2/2008 | Yasushi et al. |
| 2008/0242935 | A1 | 10/2008 | Inoue |
| 2009/0082629 | A1 | 3/2009 | Dotan et al. |
| 2009/0147531 | A1 | 6/2009 | Hsu et al. |

FOREIGN PATENT DOCUMENTS

| | | |
|---|---|---|
| JP | 06-138400 | 5/1994 |
| JP | 09-068659 | 3/1997 |
| JP | 09-294709 | 11/1997 |
| JP | 11-052257 | 2/1999 |
| JP | 11-253401 | 9/1999 |
| JP | 2004-329700 | 11/2004 |
| JP | 2006-235346 | 9/2006 |
| JP | 2007-307090 | 11/2007 |
| JP | 2008-237790 | 10/2008 |
| JP | 2008-309860 | 12/2008 |
| JP | 2009-045358 | 3/2009 |
| JP | 2009-251574 | 10/2009 |
| WO | WO 2006/004083 A1 | 1/2006 |
| WO | WO 2007/087421 A2 | 8/2007 |

OTHER PUBLICATIONS

Extended European Search Report dated Feb. 22, 2012.
United States Official Action dated Mar. 26, 2012 from related U.S. Appl. No. 13/084,055.
Notice of Allowance dated Aug. 31, 2012 from related U.S. Appl. No. 13/084,055.

ENDOSCOPE

CROSS REFERENCE TO RELATED APPLICATION

This application is a continuation application of U.S. application Ser. No. 13/084,055 filed on Apr. 11, 2011 which is a continuation application of PCT/JP2010/068724 filed on Oct. 22, 2010 and claims benefit of Japanese Application No. 2009-255187 filed in Japan on Nov. 6, 2009, the entire contents of which are incorporated herein by this reference.

BACKGROUND OF THE INVENTION

1. Field of the Invention

The present invention relates to an endoscope capable of performing front-view observation and lateral-view observation.

2. Description of the Related Art

In recent years, endoscopes provided with illumination means and observation means on a distal end side of an insertion portion have been widely used in the medical field and the like.

An endoscope is sometimes used for examining an internal wall of a tubular organ by inserting an insertion portion of the endoscope into the tubular organ. In order to facilitate such an examination, endoscopes have been developed, which have a lateral field of view in which the observation field of view is in the lateral-surface direction (lateral side) of the insertion portion, in addition to a front field of view in which the observation field of view is on the forward side of the insertion portion along the insertion direction or in the axial direction of the insertion portion.

For example, Japanese Patent Application Laid-Open Publication No. 2004-329700, as a first prior art example, discloses an endoscope having both a front observation field of view and a lateral observation field of view.

Japanese Patent Application Laid-Open Publication No. 2008-309860, as a second prior art example, discloses an optical system of an endoscope including an optical system which is rotationally symmetrical with respect to the central axis and includes a front-view optical path for picking up an image of an object in the central axis direction, and a wide-angle lateral-view optical path (lateral-view observation portion) for forming an omnidirectional (lateral-side entire circumferential) annular image outside of a circular image through the front-view optical path on the same one image pickup device by performing reflection at least twice in the annular optical element and using a part of the front-view optical path.

SUMMARY OF THE INVENTION

An endoscope according to the present invention includes: a distal end portion provided at a distal end of an insertion portion, and including a distal end surface which faces an insertion direction of the insertion portion and an outer circumferential lateral surface which faces a circumferential direction of the insertion portion; a front-view observation window for observing an insertion direction of the distal end portion, which is provided so as to face toward the insertion direction; a lateral-view observation window for observing a circumferential direction of the distal end portion, which is formed along the outer circumferential lateral surface and has a lateral observation field of view; a light-emitting member having an emission end surface for emitting light in a distal end direction of the distal end portion; a groove portion formed on the outer circumferential lateral surface of the distal end portion so as to be longer than the emission end surface of the light-emitting member along the circumferential direction of the outer circumferential lateral surface of the distal end portion and so as to be opposed to the emission end surface of the light-emitting member, the groove portion being on a proximal end side with respect to the lateral-view observation window; a plurality of particles arranged in the groove portion and having a size sufficiently smaller than a depth of the groove portion, the particles illuminating an observation field of view side of the lateral-view observation window by scattering light emitted from the emission end surface of the light-emitting member; and a transparent infill filled between the plurality of particles in the groove portion.

DETAILED DESCRIPTION OF THE PREFERRED EMBODIMENTS

Hereinafter, embodiments of the present invention will be described with reference to the drawings.

(First Embodiment)

Figure 1:
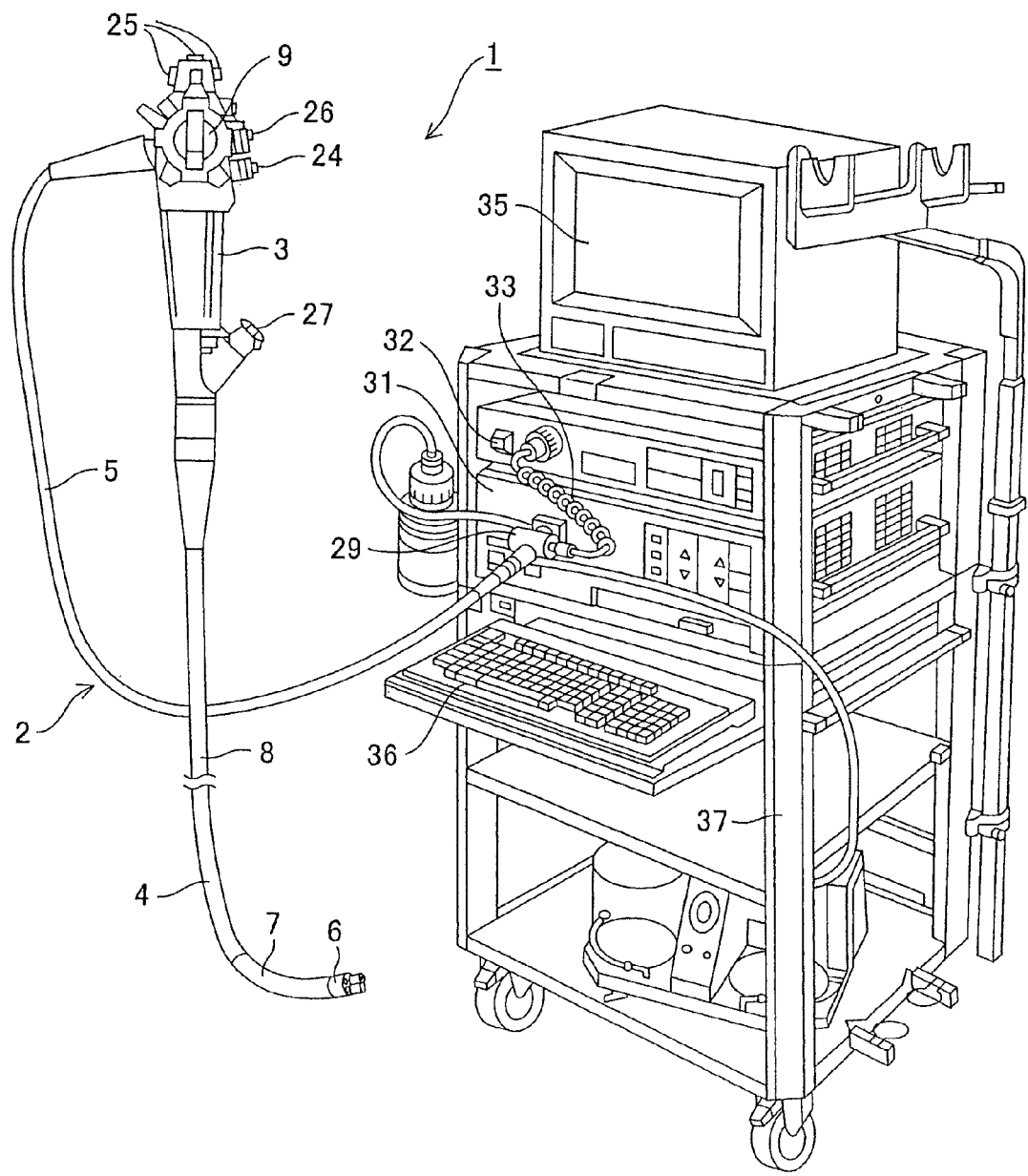
FIG. 1 is a perspective view showing an endoscope apparatus according to a first embodiment of the present invention.

As shown in FIG. 1, an endoscope apparatus 1 according to the first embodiment of the present invention includes an endoscope 2 for performing endoscopic examination. The endoscope 2 includes: an operation portion 3 adapted to be grasped by an operator for performing operation; an elongated insertion portion 4 formed on a front end of the operation portion 3 and adapted to be inserted into a body cavity and the like; and a universal cord 5, a proximal end of which is extended from a side part of the operation portion 3.

In addition, the insertion portion 4 includes: a rigid distal end portion 6 formed at a distal end thereof; a bendable bending portion 7 provided at a rear end of the distal end portion 6; and a long flexible tube portion 8 which is provided at a rear end of the bending portion 7. The bending portion 7 allows performing a bending operation using a bending operation lever 9 provided to the operation portion 3.

Figure 2:
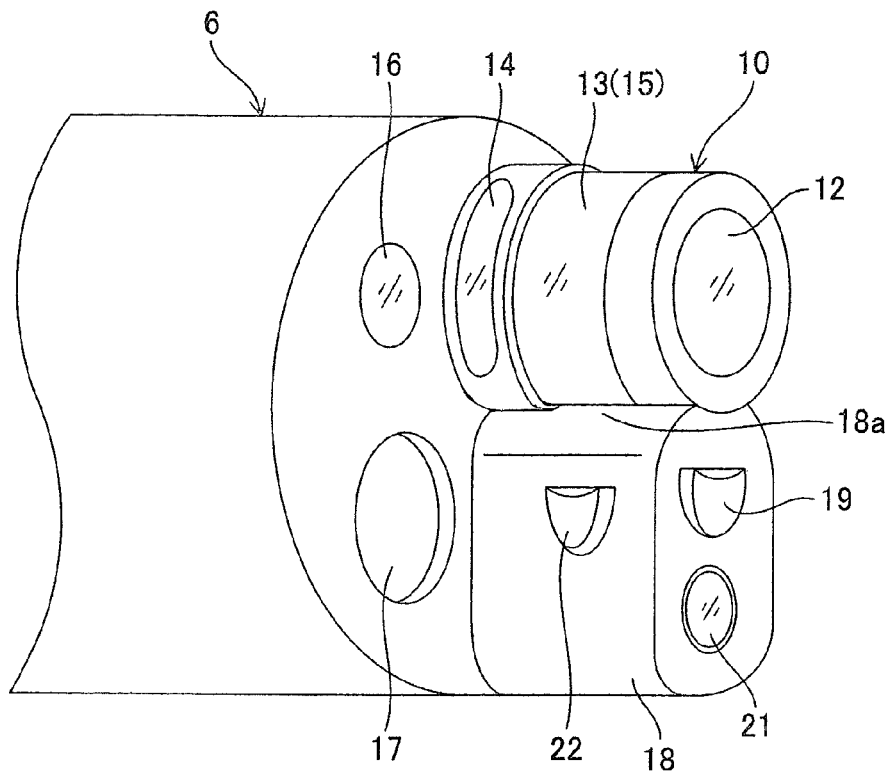
FIG. 2 is a perspective view showing a configuration of a distal end portion of an insertion portion of an endoscope.

As shown in FIG. 2, at the distal end portion 6 of the insertion portion 4, a cylindrical portion 10 as a cylindrical member is formed so as to protrude in a cylindrical shape from a position eccentric toward upper side, for example, from the center of the distal end surface of the distal end portion 6. The cylindrical portion 10 forms the distal end portion which is provided at the distal end of the insertion portion 4, and includes a distal end surface having a diameter smaller than (the outer diameter of) the insertion portion 4 and facing the insertion direction and an outer circumferential lateral surface facing the circumferential direction of the insertion portion 4, and which includes thereon a front-view observation window 12, a lateral-view observation window 13 and the like, to be described below.

Figure 3:
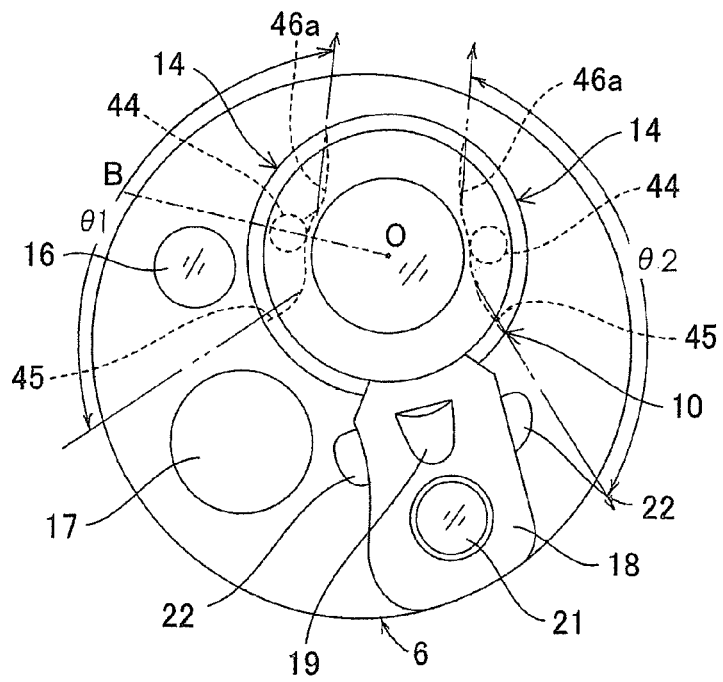
FIG. 3 is a front view showing the configuration of the distal end portion of the insertion portion.

The cylindrical portion 10 includes, on the distal end side thereof, the front-view observation window 12 as a front-view observation portion and the lateral-view observation window 13 as a lateral-view observation portion which are formed by using an objective optical system 11 (see FIG. 4) having both front-viewing and lateral-viewing functions for performing optical observation. At least one (specifically two as shown in FIG. 3) lateral-view illumination window 14 is formed as a lateral-view illumination portion near the proximal end of the cylindrical portion 10.

The lateral-view observation window 13 is formed in an annular shape along a circumferential direction of the lateral surface such that the entire circumference of the lateral surface is set as an observation field of view, for observing the cylindrically-shaped lateral-surface direction. In addition, the lateral-view observation window 13 is provided with a mirror lens 15 as a reflection optical system which captures the light from the subject to be incident from an arbitrary direction opposed to the annular shape within a lateral observation field of view (also simply referred to as field of view) to acquire the light as a lateral field-of-view image.

In addition, the distal end portion 6 includes on the distal end surface thereof: a front-view illumination window 16 through which illumination light is emitted to an observation target side in the front field of view of the front-view observation window 12, which is provided adjacent to the cylindrical portion 10; and a channel distal end opening portion 17 as an opening portion from which a treatment instrument inserted into the channel is protruded.

In the present embodiment, a supporting portion 18 is provided adjacent to the lower portion side of the cylindrical portion 10 so as to protrude from the distal end surface of the distal end portion 6.

The supporting portion 18 has a function as an optical shield for preventing a protruding member to be protruded from the distal end surface, which is not an actual observation target, from appearing within the lateral field of view so as not to be acquired as a lateral field-of-view image, and supports the cylindrical portion 10.

Furthermore, the supporting portion 18 supports a lateral-view observation window nozzle portion 22 whose distal end protrudes from the lateral surface of the supporting portion 18 and opens toward the lateral-view observation window 13, for cleaning the lateral-view observation window 13, and shields to prevent the nozzle portion from appearing on the lateral field-of-view image. Note that the lateral-view observation window nozzle portion 22 is provided at two locations as shown in FIG. 3.

The operation portion 3 shown in FIG. 1 is provided with an air-feeding/liquid-feeding operation button 24 such that cleaning air and cleaning liquid can be selectively ejected respectively from a front-view observation window nozzle portion 19 and the lateral-view observation window nozzle portion 22, and switching between air-feeding and liquid-feeding can be performed by operating the air-feeding/liquid-feeding operation button 24.

Note that FIG. 1 shows an example in which one air-feeding/liquid-feeding operation button 24 is provided. However, two buttons may be provided.

Furthermore, the operation portion 3 includes a suction operation button 26 for sucking and collecting mucus and the like in the body cavity from the channel distal end opening portion 17. Note that the channel is formed of a tube and the like, not shown, disposed in the insertion portion 4, and communicates with a treatment instrument insertion port 27 provided in the vicinity of the front end of the operation portion 3.

When performing treatment by using a treatment instrument, an operator inserts the treatment instrument from the treatment instrument insertion port 27 to allow the distal end side of the treatment instrument to protrude from the channel distal end opening portion 17, thereby allowing to perform therapeutic treatment using the treatment instrument.

Furthermore, the universal cord 5 has at a terminal end thereof a connector 29 which is to be connected to a light source apparatus 31 of the endoscope. A cap (not shown) as a connection end portion of a fluid conduit protruded from the distal end of the connector 29 and a light guide cap (not shown) as a supply end portion of illumination light are detachably connected to the light source apparatus 31, and an electric contact portion provided on a lateral surface of the connector is connected with one end of a connection cable 33.

Furthermore, a connector at the other end of the connection cable 33 is electrically connected to a video processor 32 as a signal processing apparatus which performs signal processing with respect to an image pickup device 34 (see FIG. 4) mounted to the endoscope 2.

The video processor 32 supplies a drive signal for driving the image pickup device 34 (see FIG. 4) mounted to the distal end portion 6 of the endoscope 2, and performs signal processing on an image pickup signal (image signal) outputted from the image pickup device 34 in response to the supply of the drive signal, to generate a video signal.

The video signal generated by the video processor 32 is outputted to a monitor 35 as a display apparatus, and the image picked up by the image pickup device 34 is displayed as an endoscopic image on a display surface of the monitor 35. The peripheral apparatuses such as the light source apparatus 31, the video processor 32, and the monitor 35 are disposed on a rack 37 together with a keyboard 36 through which patient information and the like are inputted.

The illumination light generated by the light source apparatus 31 is guided (transmitted) to a distal end surface side of the light guide by the light guide passing through the universal cord 5, the operation portion 3, and insertion portion 4. Distal end surfaces of the light guide which passes through the insertion portion 4 are disposed respectively at the lateral-view illumination window 14 of the cylindrical portion 10 protruded from the distal end portion 6, at the front-view illumination window 16, and at the front-view illumination window 21 (provided to the supporting portion 18), to emit the guided light.

Note that the distal end side of the light guide diverges in the insertion portion 4, for example, and one side serves as a light guide 44 in the lateral-view illumination window 14 and other sides serve as light guides, not shown, in the front-view illumination windows 16 and 21.

Then, the light is expanded from the lateral-view illumination window 14 and front-view illumination windows 16, 21, in the lateral-surface direction which is on a lateral field of view side and the distal end side of the insertion direction (also referred to as the longitudinal direction) of the insertion portion 6 which is a front field of view side, respectively, and illumination light is emitted to illuminate the observation target side in the body cavity.

Figure 4:
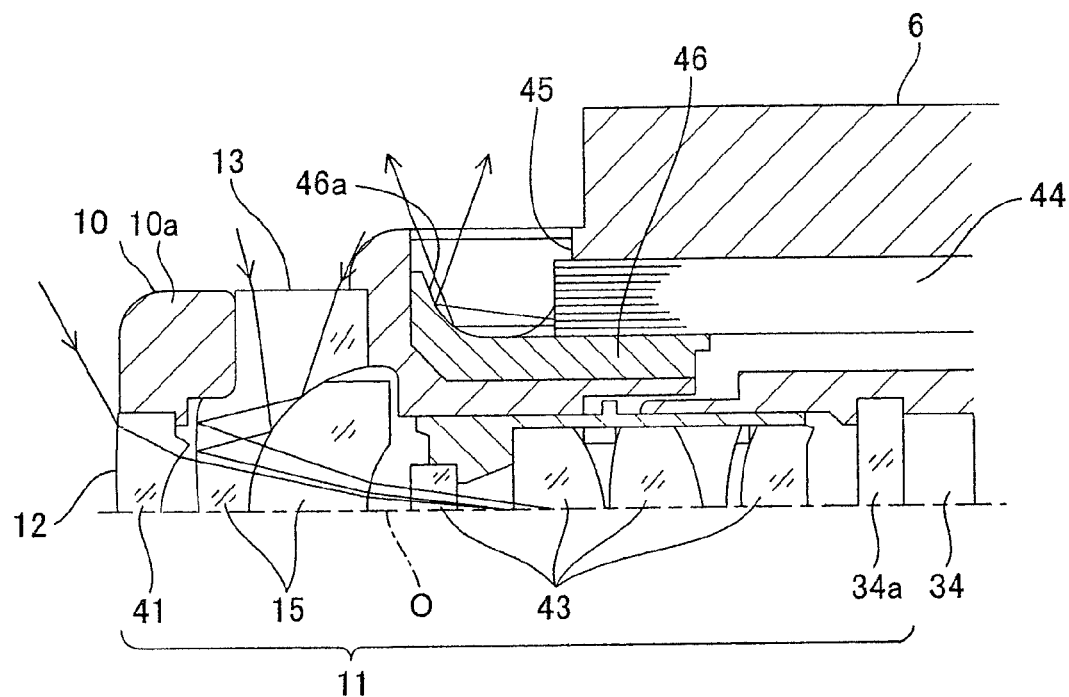
FIG. 4 is a cross-sectional view showing a structure around an objective optical system taken along an O-B cross section in FIG. 3.

FIG. 4 shows configurations of the objective optical system 11 which has both a front-view function and a lateral-view function and of the peripheral portion of the lateral-view illumination window 14, along the O-B cross section in FIG. 3.

The objective optical system 11, which forms an image on the image pickup device 34, is formed by arranging a front lens 41, a minor lens 15, and a rear lens group 43, each having a rotationally symmetric shape, on the optical axis which is coincident with the image pickup center O along the central axis of the cylindrical portion 10 protruded from the distal end portion 6. Note that a cover glass 34a is provided on the front face of the image pickup device 34. The front lens 41, the minor lens 15 and the rear lens group 43 are fixed to a lens frame in the cylindrical portion 10.

The front lens 41, which configures the objective optical system 11 and is provided to the circular front-view observation window 12, forms a wide-angle front field of view in which the distal end side of the insertion portion 4 along the insertion direction is the observation field of view.

The mirror lens 15 as a reflection optical system disposed immediately behind the front lens 41 is configured by bonding two lenses which reflect the light incident from the lateral-surface direction twice on the bonding surface and on the front surface, respectively, to guide the light toward the rear lens group 43, as shown in FIG. 4. Note that the lens part of the mirror lens 15, which is opposed to the front lens 41, also has a function for refracting the light from the front lens 41 and guiding the light toward the rear lens group 43.

By means of the mirror lens 15 provided in the lateral-view observation window 13, the lateral-view observation window 13 forms a substantially annular observation field of view which covers the entire circumference of the circumferential direction of the insertion portion, while having a predetermined viewing angle substantially centered around the optical axis in the lateral-view direction, with respect to the longitudinal axis direction of the insertion portion.

Note that FIG. 4 illustrates schematic paths of the light beam incident on the front lens 41 which forms the front-view observation window 12 from the subject side in the field of view of the front lens and the light beam incident on the mirror lens 15 which forms the lateral-view observation window 13 from the subject side in the field of view of the mirror lens.

On a center side of the image pickup surface of the image pickup device 34, the image of a subject within the front field of view set in the insertion direction is formed in a circular shape by the front lens 41 of the front-view observation window 12, and acquired as a front field-of-view image. In addition, on the image pickup surface, the image of a subject within the lateral field of view is formed in an annular shape on the outer circumferential side of the front field-of-view image by the mirror lens 15 facing the lateral-view observation window 13, and acquired as a lateral field-of-view image.

However, in the present embodiment, a shielding portion 18a, which mechanically shields the light incident from the subject side into the annular lateral field of view, is formed by the supporting portion 18. In addition, the present embodiment has a configuration in which the lateral-view illumination light emitted from the lateral-view illumination window 14 side to the lateral-surface direction is not emitted toward the supporting portion 18.

The lateral-view illumination window 14 is provided at a plurality of locations on the outer circumferential surface in the vicinity of the proximal end adjacent to the lateral-view observation window 13 of the cylindrical portion 10. In the present embodiment, as shown by the dotted lines in FIG. 3, the lateral-view illumination window 14 is provided at two locations on both left and right sides in the circumferential direction, thereby emitting the lateral-view illumination light to the entire area in the circumferential direction except the lower portion side at which the supporting portion 18 is provided.

As shown in FIG. 4, the distal end side of the light guide 44 as a light-emitting member which is arranged along the longitudinal direction of the distal end portion 6 is extended close to the proximal end of a cylindrical member 10a which forms the cylindrical portion 10 protruded from the distal end surface of the distal end portion 6. That is, a groove portion formed by a light-guiding groove 45 is equivalent to an illumination reflection portion formed by a reflection member 46 ("groove portion" ="illumination reflection portion").

The distal end surface of the light guide 44 is arranged at a position which is near the proximal end (on the outer circumferential side of the rear lens group 43) and near the lateral surface of the cylindrical portion 10. The distal end surface of the light guide 44 serves as an emission end surface for emitting the guided light, and emits the light in the distal end direction. In the present embodiment, the emission end surface has a circular shape (see FIG. 3). However, the shape is not limited to the circular shape, but may be a deformed shape including an ellipsoidal shape or a polygonal shape.

At a position where the emission end surface faces, a recessed portion 45a is provided, with the position being the center, so as to extend in an elongated manner in a strip shape along the cylindrically-shaped outer circumference of the lateral surface of the cylindrical portion 10 and form the light-guiding groove 45 as the groove portion for guiding light. The reflection member 46 as the illumination reflection portion which is formed opposed to the emission end surface is arranged in the recessed portion 45a, and on the inner surface of the reflection member 46, the light-guiding groove 45 including a reflection portion 46a for reflecting light is formed.

The reflection portion 46a (which is formed by the reflection member 46) arranged on the inner surface of the light-guiding groove 45 has a substantially semispherical recessed surface in the vertical cross section shown in FIG. 4. Furthermore, the semispherical recessed surface of the reflection portion 46a is formed so as to be longer than the emission end surface of the light guide 44, along the circumferential direction of the cylindrical portion 10.

The reflection portion 46a reflects the light emitted from the emission end surface toward the distal end side of the distal end portion 6 by the reflection portion 46a to change the advancing direction of the light into the lateral-surface direction, and guides the light in a wide range of the lateral-surface direction along the circumferential direction, to emit the light from the lateral-view illumination window 14, thereby illuminating the observation field of view side (observation target side) of the lateral-view observation window 13. Therefore, the light emitted from the light-guiding groove 45 in the lateral-surface direction becomes lateral-view illumination light.

Note that the reflection portion 46a can be formed by arranging a metal thin film having a high reflectance made of aluminum, chrome, nickel chrome, silver, gold and the like on the inner surface of the reflection member 46.

In the present embodiment, the reflection member 46 is thus arranged in the recessed portion 45a such that the light-guiding groove 45 including the reflection portion 46a is formed in an elongated manner along the outer circumference of the lateral surface of the cylindrical portion 10. In addition, the light guide 44 as a light-emitting member is arranged such that the emission end surface thereof is located near the center position in the circumferential direction of the reflection member 46 (or the light-guiding groove 45).

Figure 5:
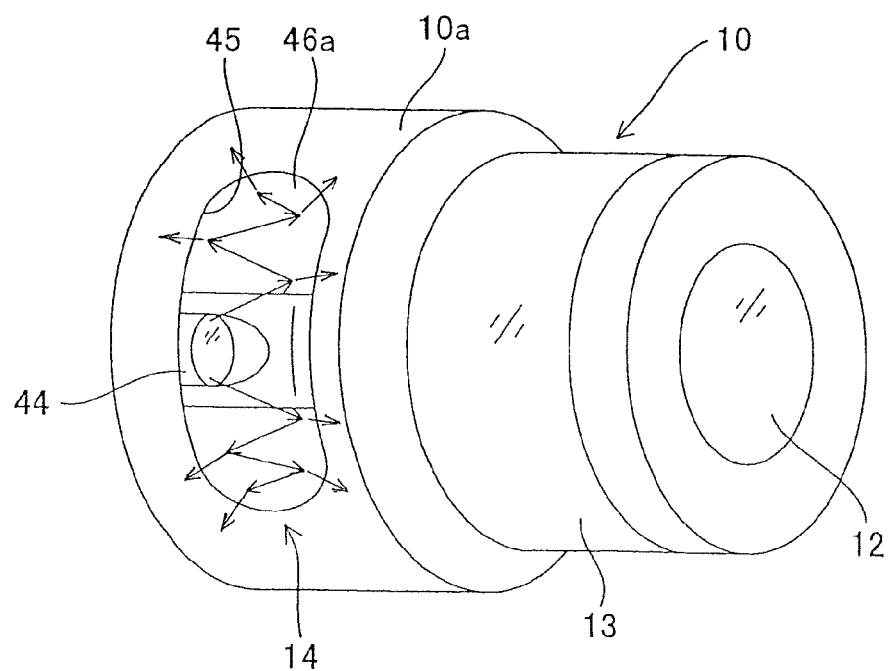
FIG. 5 is an illustration diagram showing the situation in which the light emitted from an emission end surface of a light guide constituting a lateral-view illumination window is reflected by a reflection portion to perform wide-angle lateral-view illumination.

The light emitted from the emission end surface of the light guide 44 is reflected by the reflection portion 46a arranged so as to form a reflection surface around the emission end surface, thereby allowing the illumination light to be emitted laterally over a wide range from the lateral-view illumination window 14 to which the light-guiding groove 45 is provided. FIG. 5 shows a situation in which the lateral-view illumination light is emitted from the lateral-view illumination window 14. Note that FIG. 5 illustrates a state where the supporting portion 18 is not provided. Also FIG. 7 or subsequent drawings thereafter shows the cylindrical portion 10 in a state where the supporting portion 18 is not provided.

As shown in FIG. 5, the light emitted from the emission end surface of the light guide 44 is expanded from the inner portion of the lateral-view illumination window 14 to the outside opposed to the lateral-view illumination window 14 by repeating one-time reflection or plural times of reflection by the reflection portion 46a having the recessed surface shape, and emitted as lateral-view illumination light.

In this case, as described above, the lateral-view illumination light can be emitted over a wider range than the range in the circumferential direction where the lateral-view illumination window 14 is formed, by repeating one-time reflection or plural times of reflections by the reflection portion 46a having the recessed surface shape.

Similarly, by repeating one-time reflection or plural times of reflections by the reflection portion 46a having the recessed surface shape, it is possible to emit the lateral-view illumination light which covers a predetermined viewing angle substantially centered around the optical axis in the lateral-view direction with respect to the longitudinal direction of the column of the cylindrical portion 10, that is, covers from the forward side of the cylindrical portion 10 to the rearward side of the cylindrical portion 10. Furthermore, the light guide 44 and the light-guiding groove 45 including the reflection portion 46a or reflection member 46, each of which is provided at two locations, enable the lateral-view illumination light to be emitted over a wide range which almost covers the entire circumference in the lateral-surface direction, except the lower side portion of the lateral surface of the cylindrical portion 10, for example.

FIG. 3 schematically shows, by the two-dot-chain lines, the ranges (angles θ1, θ2) of the lateral-view illumination lights emitted respectively from the two lateral-view illumination windows 14 along the lateral-surface direction. Note that the illumination ranges toward the lower portion side can be made wider than the ranges (angles θ1, θ2) by changing the length of each of the light-guiding grooves 45 in the circumferential direction in FIG. 3.

The illumination lights emitted from the lateral-view illumination windows 14 formed long along the lateral-surface direction enable the lateral-view illumination over a wide range corresponding to the wide-angle field of view which can be observed by the lateral-view observation window 13.

The endoscope 2 having such a configuration according to the present embodiment includes: the cylindrical portion 10 as the distal end portion which is provided at the distal end of the insertion portion 4 and which includes a distal end surface facing the insertion direction of the insertion portion 4 and the outer circumferential lateral surface facing the lateral-surface direction of the insertion portion 4; the front-view observation window 12 for observing the insertion direction of the cylindrical portion 10, which is provided so as to face the insertion direction; and the lateral-view observation window 13 for observing the lateral-surface direction of the cylindrical portion 10, which is formed along the circumferential direction of the lateral surface and has a wide range of lateral field of view.

Furthermore, the endoscope 2 includes: the light guide 44 as the light-emitting member having the emission end surface for emitting light in the distal end direction of the cylindrical portion 10; and, on the side closer to the proximal end than the lateral-view observation window 12, the reflection member 46 as the illumination reflection portion which has the reflection portion 46a formed so as to be longer than the emission end surface of the light guide 44 along the circumferential direction of the outer circumferential lateral surface of the cylindrical portion 10, and which reflects the light emitted from the emission end surface of the light guide 44 in the lateral-surface direction of the cylindrical portion 10 by means of the light emission portion 46a, to illuminate the observation field of view side of the lateral-view observation window 13.

As described above, the lateral-view illumination window 14 provided at the two locations enables the lateral-view illumination corresponding to the lateral-view observation window 13 having a wide range of observation field of view in the circumferential direction.

Figure 6:
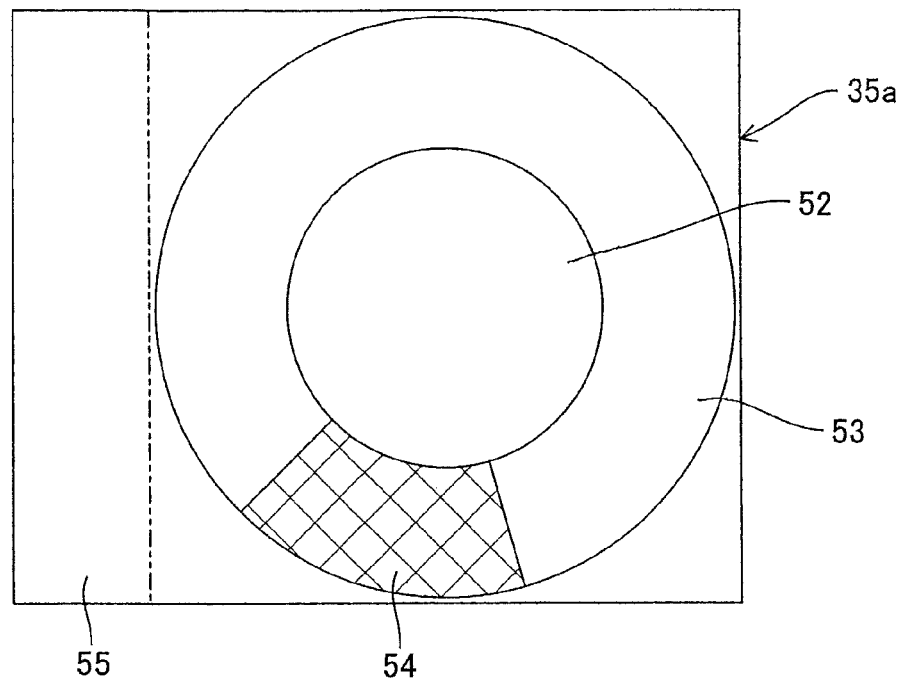
FIG. 6 is a view showing one example of an endoscopic image according to the first embodiment.

FIG. 6 illustrates a display example in which the endoscope 2 is used to display the subject image picked up by the image pickup device 34 as an endoscopic image on a display surface 35a of the monitor 35.

A rectangular area 51 in FIG. 6 corresponds to a display area on the image pickup surface of the image pickup device 34. The circular area in the center of the rectangular area 51 is a display area 52 of the front field-of-view image by the front-view observation window 12, and a ring-shaped area outside the display area 52 is a display area 53 of the lateral field-of-view image by the lateral-view observation window 13.

In addition, an area which shields a part of the lower portion side of the lateral field of view by the shielding portion 18a formed at the supporting portion 18 is a black area 54 in the lateral field-of-view image. The black area 54 is an image non-display area where no image is displayed.

The present embodiment thus enables the wide range of lateral-view illumination with which a lateral field-of-view image of a wide angle of equal to or larger than three-quarters of the entire circumference can be acquired.

In addition, the present embodiment is configured to reflect light by the reflection member 46 or the reflection portion 46a provided on the inner surface of the light-guiding groove 45 without bending the emission end surface side of the light guide 44 in the lateral-surface direction and emit the illumination light in the lateral-surface direction, thereby enabling to reduce the diameter of the cylindrical portion 10 located on the distal end side of the insertion portion 4.

Furthermore, the operator can smoothly examine of a tubular organ and the like by observing the endoscopic image.

According to the endoscope 2 of the present embodiment, when the lateral-view observation window 13 having a wide range of lateral field of view in the circumferential direction is also used in addition to the front field of view, it is possible to exhibit an effect of enabling a wide range of lateral-view illumination corresponding to the wide range of lateral field of view to be performed. Furthermore, in this case, the front-view illumination windows 16, 21 as the front-view illumination portions can illuminate the observation field of view side of the front-view observation window 12.

Therefore, according to the endoscope 2 of the present embodiment, it is possible to acquire an endoscopic image by front-view observation and wide-angle lateral-view observation. As a result, the operator can smoothly examine a tubular organ and the like by observing the endoscopic image.

In addition, according to the present embodiment, the lateral-view illumination window 14, which forms the lateral-view illumination portion (or illumination reflection portion) adjacent to the lateral-view observation window 13 formed in an annular shape on the cylindrical portion 10, is formed in a substantially strip shape in parallel with the annular lateral-view observation window 13, thereby allowing to efficiently illuminate the observation field of view side of the lateral-view observation window 13.

In addition, according to the present embodiment, the cylindrical portion 10 can be formed in a column shape, a diameter of which is made further smaller than that of the distal end portion 6 of the insertion portion 4. Such a configuration facilitates a smooth insertion of the insertion portion 4 at the time of insertion into a body cavity.

Furthermore, the diameter of the cylindrical portion 10 is made smaller than that of the distal end portion 6, which prevents the lateral-view observation window from contacting a tube wall, thereby facilitating the observation. In addition, even in a case of insertion into a thin tubular cavity, the distance between the tube wall and the lateral-view illumination portion can be ensured, thereby enabling the illumination light in the lateral-view direction to be illuminated over a wider range.

Note that, when a wide range of lateral-view illumination is performed in a circumferential direction, it is preferable to illuminate almost the entire circumference. However, even in the present embodiment having a configuration in which the protruding member is light-shielded, it is possible to perform a lateral-view illumination over a wide range equal to or larger than three-quarters of the entire circumference, as described above. In addition, though the above-described first embodiment includes the supporting portion 18 provided with the shielding portion 18a, the embodiment may have a configuration without the shielding portion 18a and the supporting portion 18 to enable a wider range of observation and illumination in the lateral-surface direction. In this case, the cylindrical portion 10 may be formed at the center position of the distal end portion 6.

Figure 7:
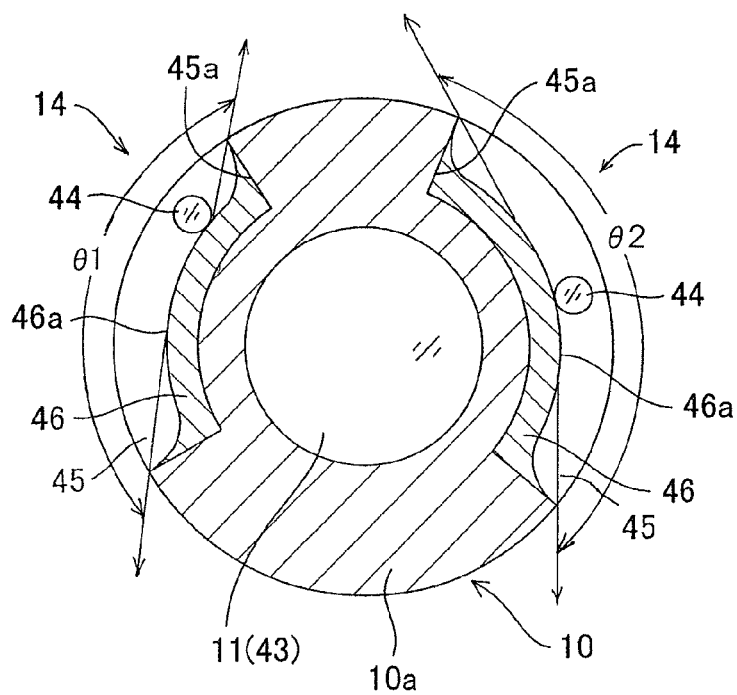
FIG. 7 is a cross-sectional view showing a structure of a cylindrical portion according to a first modified example of the first embodiment.

FIG. 7 shows a configuration of a lateral-view illumination portion according to a first modified example of the first embodiment by using a cross-sectional view of the cylindrical portion 10. FIG. 7 shows a configuration of the lateral-view illumination windows 14 which are arranged on the left and right respectively in the case where the front view of the cylindrical portion 10 in FIG. 3 is cut along a horizontal section in the vicinity of the emission end surface of the light guide 44.

The present modified example is configured similarly to the first embodiment but the light guide 44 of the one lateral-view illumination window 14 (left side) is eccentric from the center position in the circumferential direction of the reflection member 46 and arranged at a position close to an end, for example. In addition, in the present modified example, the lengths of the light-guiding grooves 45 are made longer in the circumferential lateral-surface direction than in the first embodiment, thereby achieving wider illumination ranges ($\theta1$, $\theta2$).

Note that the circular portion at the center of the cylindrical portion 10 indicates the rear lens group 43 configuring the objective optical system 11, and the image pickup device 34 (not shown) is arranged at a rearward position of the rear lens group 43. In addition, the present modified example has a configuration in which the supporting portion 18 is omitted from the first embodiment. Other configurations are almost the same as those in the first embodiment.

The present modified example has basically the same working and effects as those in the first embodiment. Furthermore, the position of the emission end surface of the light guide 44 as a light-emitting member is eccentric, thereby allowing to adjust the light amount distribution of the illumination light in the case of illuminating in the circumferential direction.

For example, in the case shown in FIG. 7, the lateral-view illumination windows 14 are not provided at the upper portion of the cylindrical portion 10. Therefore, by arranging the light guide 44 disposed in one of the lateral-view illumination windows 14, at a position closer to the upper side, as shown in FIG. 7, the upper side light amount of the lateral-view illumination light can be increased. Therefore, according to the present modified example, adjustment is possible for performing illumination suitable for the lateral-view observation.

Figure 13:
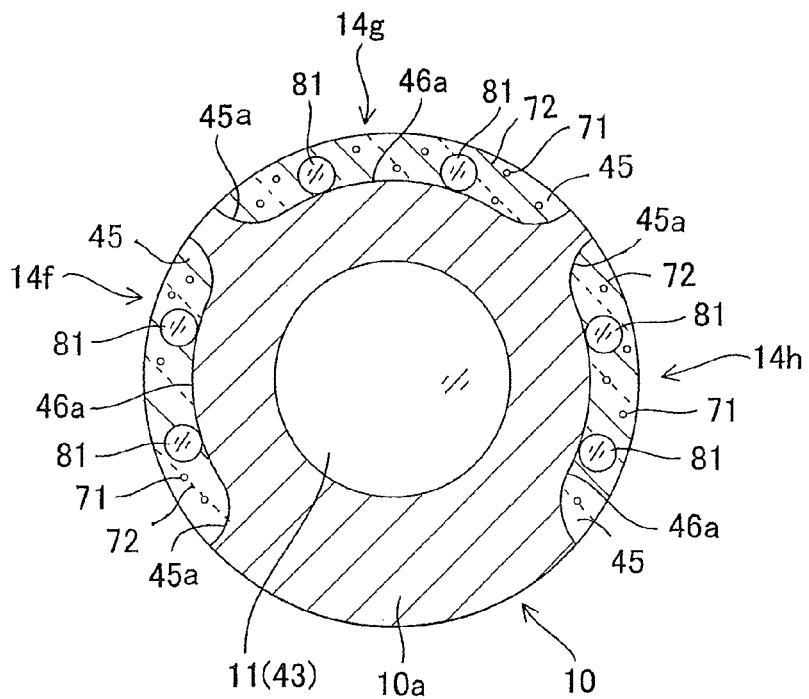
FIG. 13 is a cross-sectional view showing a structure of a cylindrical portion according to a second modified example of the third embodiment of the present invention.

In addition, as shown in FIG. 13 to be described later, the light-guiding groove 45 may be directly formed on the cylindrical member 10a (without using the reflection member 46).

Figure 8:
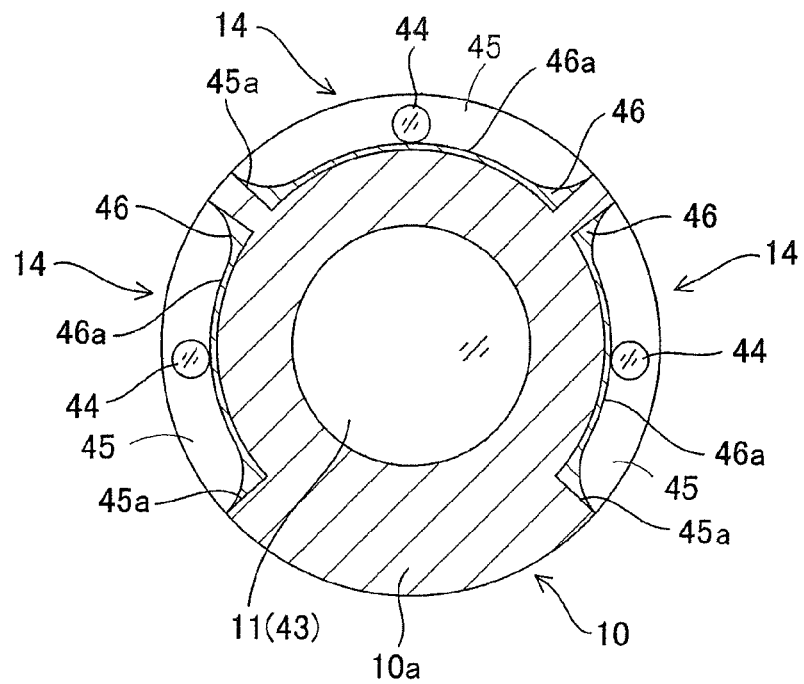
FIG. 8 is a cross-sectional view showing a structure of a cylindrical portion according to a second modified example of the first embodiment.

FIG. 8 shows a configuration of a lateral-view illumination portion according to a second modified example of the first embodiment by using a cross-sectional view. In the present modified example, the lateral-view illumination window 14 provided at two locations in the first embodiment is provided at three locations.

Similarly as in the first embodiment, each of the lateral-view illumination windows 14 is configured such that the reflection member 46 including the reflection portion 46a or the light-guiding groove 45 is arranged along the circumferential direction, and near the center thereof, the emission end surface of the light guide 44 is arranged.

The present modified example has the same effects as those in the first embodiment, and compared with the case where the lateral-view illumination window is provided at two locations, the observation target side in the lateral observation field of view of the lateral-view observation window 13 can be illuminated over a wider range and with increased illumination light amount.

Figure 9:
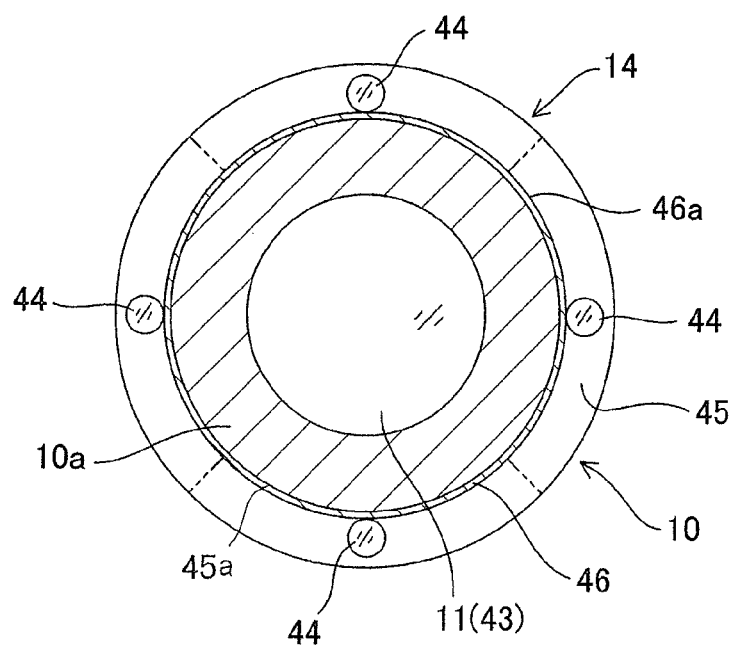
FIG. 9 is a cross-sectional view showing a structure of a cylindrical portion according to a third modified example of the first embodiment.

FIG. 9 shows a configuration of a lateral-view illumination portion according to a third modified example of the first embodiment by using a cross-sectional view. In the present modified example, the lateral-view illumination window 14 provided at two locations in the first embodiment is provided at four locations.

Furthermore, in the present modified example, the light-guiding groove 45 is provided so as to cover the entire circumference of the columnar lateral surface. Therefore, the reflection member 46 having the reflection portion 46a is provided in the recessed portion 45a which is formed on the entire circumference of the columnar lateral surface of the cylindrical portion 10. Note that the reflection member 46 or the light-guiding groove 45 may be a single component covering the entire circumference. However, the reflection member 46 or the light-guiding groove 45 may be divided at the positions shown by the two-dot-chain lines, for example, and provided in plurality (four in this case).

The present modified example has almost the same effects as those in the first embodiment, and similarly in the second modified example, the lateral-surface direction can be illuminated over a wider range and with increased illumination light amount, compared with the case where the lateral-view illumination window is provided at two locations. Furthermore, in this case, it is also possible to perform illumination which more uniformly covers the entire circumference in the lateral-surface direction.

Note that the third modified example shown in FIG. 9 may be further modified to change the number of the light guides 44 to be arranged as the light-emitting members, for example. The number of the light guides 44 may be three similarly as in the second modified example, or the number of the light guides 44 may be five or more, for example.

(Second Embodiment)

Figure 10:
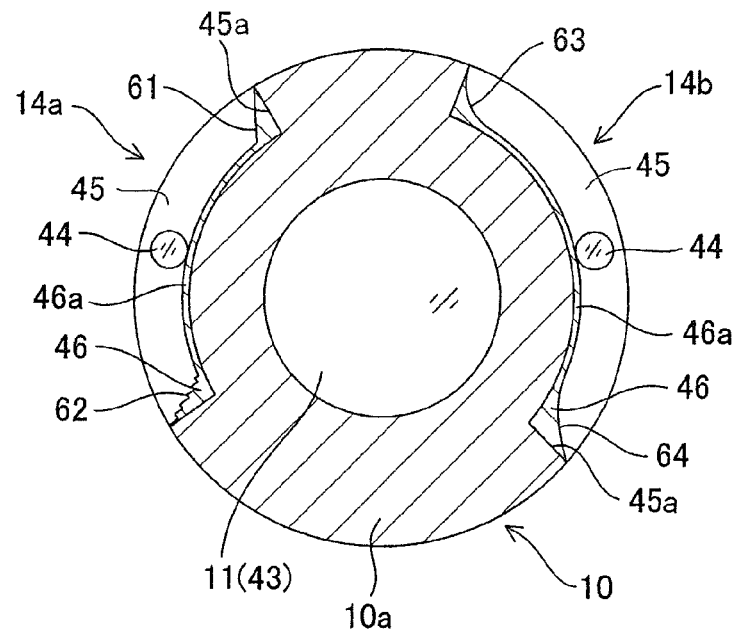
FIG. 10 is a cross-sectional view of a cylindrical portion according to a second embodiment of the present invention.

Next, the second embodiment of the present invention will be described. FIG. 10 shows a configuration of a lateral-view illumination portion according to a second embodiment of the present invention by using a cross-sectional view.

According to the lateral-view illumination portion of the present embodiment, for example, one of the lateral-view illumination windows 14 in the lateral-view illumination portion according to the first embodiment is configured as a lateral-view illumination window 14a in which both end portions in the circumferential direction of the reflection portion 46a provided on the inner surface of the reflection member 46 (light-guiding groove 45) are formed as a planar reflection surface 61 and a stepped reflection surface 62, respectively.

Furthermore, in the present embodiment, the other of the lateral-view illumination windows 14 according to the first embodiment is configured as a lateral-view illumination window 14b in which both end portions in the circumferential direction of the reflection portion 46a provided on the inner surface of the reflection member 46 are formed as a spherical reflection surface 63 and an aspherical (curved-surface) reflection surface 64, respectively. The spherical reflection surface 63 is formed in a spherical shape (within a range smaller than a semisphere) and the aspherical (curved-surface) reflection surface 64 is formed in an aspherical shape.

The reflection surfaces in the present embodiment may be formed by using a metal thin film made of aluminum, chrome, nickel chrome, silver, gold and the like, similarly to the above-described reflection portion 46a. Note that the present embodiment may be applied to the configuration of the first embodiment in which the supporting portion 18 is provided with a shielding portion 18a or to the configuration without the supporting portion 18. Other configurations are the same as those in the first embodiment.

The present embodiment has the same effects as those in the first embodiment.

Furthermore, according to the present embodiment, it is possible to form lateral-view illumination means having illumination characteristics suitable for an intended use or targeted illumination characteristics by combining the reflection surfaces each having a different reflection characteristic.

When the planar reflection surface 61 is provided, for example, the distribution of the illumination light amount for illuminating the upper side of the cylindrical portion 10 can be adjusted by adjusting the angle at which the reflection surface is arranged (angle at which the reflection surface erects diagonally from the bottom surface side, for example). Note that the planar reflection surface 61 may be formed as a roughened surface and the like which is prone to irregularly reflect light, instead of a mirror surface.

In addition, when the stepped reflection surface 62 is formed, it is possible to provide a characteristic in which the light amount distribution of the emitted illumination light spreads more widely compared with the planar reflection surface. The pitch value of the steps in this case may be adjusted or the stepped surface itself may be provided on a curved surface.

In addition, when the spherical reflection surface 63 is formed, the distribution of the illumination light amount in a different direction in the lateral-surface direction can be continuously adjusted. Furthermore, when the aspherical (curved surface) reflection surface 64 is formed, it is possible to achieve the light amount distribution, the spread of which in a desired direction is adjusted further than the case of the spherical reflection surface 63.

The present embodiment thus enables the lateral side to be illuminated over a wider range and uniformly by adjusting a plurality of reflection surfaces having different reflection characteristics.

Note that, in FIG. 10, description has been made on the example in which the four reflection surfaces 61 to 64, each of which has a characteristic different from each other, are provided to the lateral-view illumination windows 14a, 14b. However, the present embodiment is not limited to the example shown in FIG. 10. For example, only one reflection surface of the four reflection surfaces 61 to 64 shown in FIG. 10 may be applied to the lateral-view illumination window 14 according to the first embodiment. Alternatively, two or three reflection surfaces may be combined and applied.

In addition, the present embodiment is described assuming the case where the present embodiment is applied to the first embodiment, for example. However, the present embodiment may be applied to the modified examples of the first embodiment.

(Third Embodiment)

Figure 11:
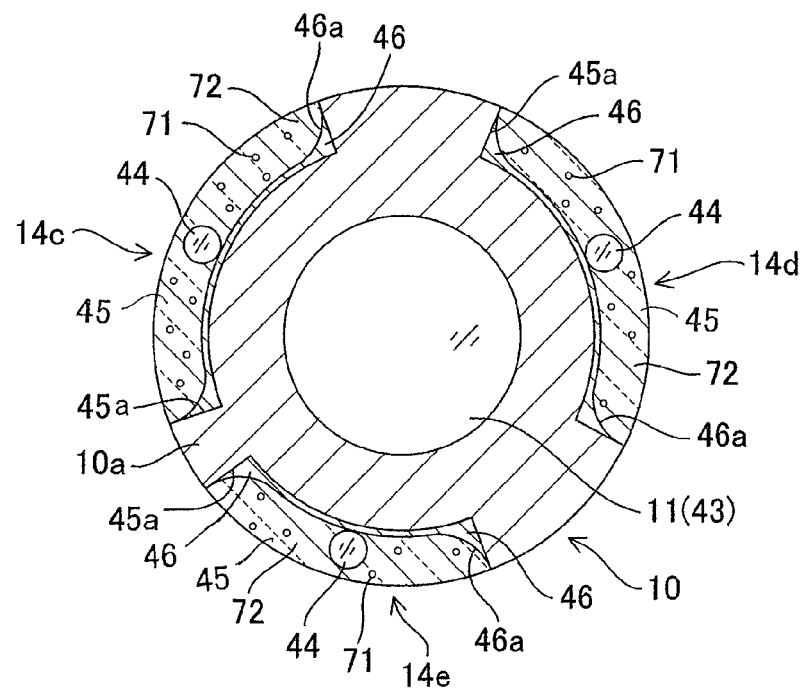
FIG. 11 is a cross-sectional view showing a cylindrical portion according to a third embodiment of the present invention.

FIG. 11 shows a configuration of a lateral-view illumination portion according to the third embodiment of the present invention by using a cross-sectional view. In the present embodiment, three lateral-view illumination windows 14c, 14d, and 14e are provided similarly as in the second modified example shown in FIG. 8, for example. However, FIG. 11 shows an arrangement example different from that shown in FIG. 8.

In the configuration of the lateral-view illumination window 14 shown in FIG. 8, each of the lateral-view illumination windows 14c, 14d, and 14e forms a light-guiding member by filling inside of the light-guiding groove 45 with a light-scattering material 71 made of glass particles and the like as a light-scattering member for scattering light, and a transparent infill 72.

Note that, the infill 72 has a function for holding the light-scattering material 71 in a moderate distribution or density such that the entire light-scattering material 71 has a function for substantially uniformly scattering light in the light-guiding groove 45. In addition, the light-scattering material 71 has a function as a reflection portion which reflects light by means of scattering. Furthermore, the size of the diameter of the glass particles and the like as the light-scattering member is sufficiently small compared with the depth size of the light-guiding groove 45.

The light-guiding member has a function of uniformly surface-emitting the light emitted from the emission end surface of the light guide 44 as the light-emitting member from each of the end surfaces (as emitting end surfaces of the illumination light) of the lateral-view illumination windows 14c, 14d, and 14e by repeating light scattering by the light-scattering material 71.

The present embodiment may have a configuration in which the reflection portion 46a is provided at the inner surface part of the reflection member 46 configuring the light-guiding groove 45, or a configuration in which the reflection portion is not provided. As shown in FIG. 11, it is preferable to provide the reflection portion 46a at a part of the light-guiding groove 45 which is near the lateral surface of the emission end surface of the light guide 44.

The light-scattering material 71 is not limited to be configured of small glass particles but may be configured of resin particles, metal particle, or the like. In addition, the glass particles and the like configuring the light-scattering material 71 may have either a hollow shape or a solid shape.

The present embodiment thus allows the direction of the light emitted from each of the emission end surfaces of the light guides 44 to be changed, thereby enabling lateral-view illumination light to be uniformly emitted from each of the lateral-view illumination windows 14c, 14d, and 14e toward outside of the lateral-view illumination windows 14c, 14d, and 14e.

Therefore, according to the present embodiment, it is possible to uniformly illuminate an observation target on the observation field of view side on the lateral side of the lateral-view observation window 13, thereby allowing to acquire an endoscopic image in which easily observable excellent lateral field-of-view image can be acquired. Therefore, an operator can smoothly perform endoscopic examination by observing the endoscopic image. In addition, the present embodiment has also the same effects as those in the first embodiment.

Note that, in the configuration shown in FIG. 11, only light-scattering material 71 having a moderate film thickness may be provided inside of the light-guiding groove 45, for example. In this case, the light-scattering material 71 may be provided in a band shape along each of the lateral-view illumination windows 14c, 14d, and 14e. Also in this configuration, it is possible to substantially uniform the illumination light emitted from each of the lateral-view illumination windows 14c, 14d, and 14e by repeating light scattering using the light-scattering material 71 to allow the uniformed light to be emitted in the lateral-surface direction.

When only the light-scattering material 71 is provided, the light-scattering material 71 may be formed along the inner surface of the light-guiding groove 45. Also in this case, it is possible to achieve a function similar to that of the above-described light-guiding member. In this configuration, the reflection portion 46a may be omitted.

Figure 12:
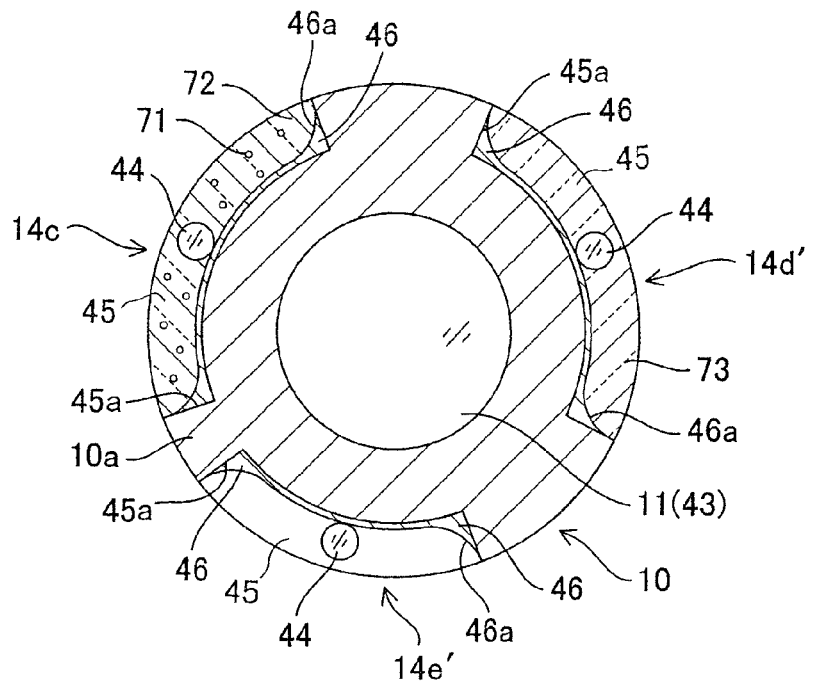
FIG. 12 is a cross-sectional view showing a structure of a cylindrical portion according to a first modified example of the third embodiment of the present invention.

FIG. 12 shows a configuration of a lateral-view illumination portion according to a first modified example of the third embodiment by using a cross-sectional view. The present modified example shows an example in which lateral-view illumination windows each having a different characteristic are provided in the third embodiment shown in FIG. 11.

For example, the lateral-view illumination window 14d in FIG. 11 is modified as a lateral-view illumination window 14d' filled with a transparent infill 73 such as glass and resin, instead of the light-scattering material 71 and the infill 72.

In addition, the lateral-view illumination window 14e in FIG. 11 is modified as a lateral-view illumination window 14e' in which the light-scattering material 71 and the infill 72 are not provided. The lateral-view illumination window 14e' may have the same configuration as that of the lateral-view illumination window 14c or 14d.

According to the present modified example, at least one of the plurality of lateral-view illumination windows provided in the circumferential direction of the cylindrical portion 10 can perform uniform surface illumination similarly as in the case of the third embodiment. In addition, when the lateral-view illumination window 14d' filled with the infill 73 is formed, the outer circumferential surface thereof can be formed in an annular shape without a recessed portion. Other than the above, the present modified example has the same effects as those in the first embodiment.

FIG. 13 shows a configuration of a lateral-view illumination portion according to a second modified example of the third embodiment by using a cross-sectional view. In the present modified example, the three lateral-view illumination windows 14 shown in FIG. 8 are modified to include a light-emitting member using a light-emitting diode (LED) 81 instead of the light guide 44 (configured by a light guide fiber (bundle)), for example. In addition, in the present modified example, the light-guiding groove 45 is directly formed in the cylindrical member 10a, and the reflection portion 46a is provided on the inner surface of the light-guiding groove 45. In this case, the light-guiding groove 45 functions also as the reflection member 46 having the reflection portion 46a.

Furthermore, in the present modified example, each of lateral-view illumination windows 14f, 14g, and 14h is formed by arranging a plurality of LEDs 81 in one of the light-guiding grooves 45.

In addition, in the present modified example, the light-scattering material 71 and the infill 72 are also filled in each of the light-guiding grooves 45 to form a light-guiding member.

According to such a configuration, the present modified example has the effect of enabling uniform lateral-view illumination and an increase in the illumination light amount in the lateral-surface direction, similarly as in the third embodiment.

Note that an LD, an organic electroluminescence (organic EL), or inorganic EL may be used instead of the LED 81.

Furthermore, the configuration described with reference to FIG. 13 may be applied to other embodiments or other modified examples described above. For example, a light-emitting member such as the LED 81, the LD, the organic EL, and the inorganic EL may be used instead of the light guide 44 in the first embodiment.

In addition, a plurality of light-emitting members may be arranged in one lateral-view illumination window as shown in FIG. 13 with respect to the first embodiment and the like.

In addition, as shown in FIG. 13, the light-guiding groove 45 may be directly formed in the cylindrical member 10a (without using the reflection member 46), and the reflection portion 46a made of a metal thin film such as of aluminum may be formed on the inner surface such as the bottom surface or the lateral surface of the light-guiding groove 45.

Note that when lateral-view illumination is performed, the lateral-view illumination of a wide angle of three-quarters of the entire circumference can be achieved as in the above-described first embodiment. However, the present invention is not limited to the case, and can be widely applied to a case of lateral-view illumination of a wide angle larger than a predetermined angle (for example, 180 degrees).

Also embodiments configured by partly combining the above-described embodiments also belong to the present invention.

What is claimed is:

1. An endoscope comprising:
   a distal end portion provided at a distal end of an insertion portion, and including a distal end surface which faces an insertion direction of the insertion portion and an outer circumferential lateral surface which faces a circumferential direction of the insertion portion;
   a front-view observation window for observing an insertion direction of the distal end portion, which is provided so as to face toward the insertion direction and has a front observation field of view;
   a lateral-view observation window for observing a circumferential direction of the distal end portion, which is formed along the outer circumferential lateral surface and has a lateral observation field of view;
   a cylindrical portion provided in a cylindrical shape at a predetermined part of the distal end portion;
   a light-guiding member for guiding light from a proximal end side of the insertion portion to the cylindrical portion, the light-guiding member including an emitting end surface from which the light is emitted;
   a groove portion including a groove for guiding light emitted from the light-guiding member, the groove being formed along an outer circumferential lateral surface of the cylindrical portion;
   an illumination reflection portion which is opposed to the emission end surface of the light-guiding member and provided in the groove portion, the illumination reflection portion reflecting light from the light-guiding member to an outer circumferential side of the cylindrical portion; and
   a lateral-view illumination window which his provided on the outer circumferential lateral surface of the cylindrical portion, the lateral-view illumination window emitting the light reflected by the illumination reflection portion in a circumferential direction of the cylindrical portion.

2. The endoscope according to claim 1, wherein the cylindrical portion is smaller than the insertion portion in diameter.

3. The endoscope according to claim 1, further comprising a plurality of particles arranged in the groove portion and having a size sufficiently smaller than a depth of the groove portion, the particles illuminating an observation field of view side of the lateral-view observation window by scattering light emitted from the emission end surface of the light-guiding member.

4. The endoscope according to claim 3, further comprising a transparent infill filled between the plurality of particles in the groove portion.

5. The endoscope according to claim 1, further comprising:
   an image pickup device for picking up an image of a subject; and
   an objective optical system including:
      a first lens arranged along a central axis of the cylindrical portion, the first lens forming an image of a subject in the insertion direction;
      a second lens arranged behind the first lens, the second lens forming an image of the subject in the insertion direction which passed through the first lens and an image of a subject in the circumferential direction; and
      a rear lens arranged between the second lens and the image pickup device.

6. The endoscope according to claim 5, wherein, a proximal end side of the second lens, the lateral-view observation window and the groove portion are formed.

7. The endoscope according to claim 5, wherein the rear lens is a lens group including a plurality of lenses.

8. The endoscope according to claim 5, wherein the objective optical system forms an optical image of the subject incident from the front-view observation window in a circular area on a center side of the image pickup surface of the image pickup device, and forms an optical image of the subject incident from the lateral-view observation window in an annular area outside of the circular area.

9. The endoscope according to claim 5, wherein
   the first lens is a lens having a rotationally symmetric shape for guiding light incident from the front-view observation window to the proximal end side of the insertion portion;
   the second lens is a lens having a rotationally symmetric shape, which is arranged along an optical axis of the first lens and on a proximal end side of the insertion portion with respect to the first lens, refracts light from the first lens and guide the refracted light to the proximal end side of the insertion portion, causes light incident from the lateral-view observation window to be reflected twice by two surfaces, and guides the reflected light to the proximal end side of the insertion portion; and
   the rear lens is arranged along an optical axis of the second lens and on a proximal end side of the insertion portion with respect to the second lens, the rear lens causing the subject image in the front observation field of view to be formed on the image pickup device, and causing the subject image in the lateral observation field of view to be formed on an outer circumferential side of the subject image in the front observation field of view of the image pickup device.

10. The endoscope according to claim 1, wherein the lateral-view observation window has a lateral field-of-view of a wide angle larger than at least three-quarters of an entire circumference along a circumferential direction of a lateral surface of the cylindrical portion, and the lateral-view illumination window enables wide range of lateral-view illumination larger than at least three-quarters of the entire circumference along a circumferential direction of a lateral surface of the distal end portion.

11. The endoscope according to claim 1, wherein the cylindrical portion is pro-vided so as to protrude in a longitudinal direction of the distal end portion from a circular distal end surface of the distal end portion.

* * * * *